(12) United States Patent
Araya

(10) Patent No.: US 9,248,004 B2
(45) Date of Patent: Feb. 2, 2016

(54) ULTRASONIC TIP FOR MINIMALLY INVASIVE CROWN LENGTHENING

(75) Inventor: Jorge Antonio Jofré Araya, San Pedro de la Paz (CL)

(73) Assignee: Jorge Antonio Jofré Araya, San Pedro de la Paz (CL)

( * ) Notice: Subject to any disclaimer, the term of this patent is extended or adjusted under 35 U.S.C. 154(b) by 0 days.

(21) Appl. No.: 13/112,688

(22) Filed: May 20, 2011

(65) Prior Publication Data

US 2011/0295294 A1 Dec. 1, 2011

(30) Foreign Application Priority Data

May 20, 2010 (CL) .......................................... 00519

(51) Int. Cl.
*A61C 3/03* (2006.01)
*A61B 17/32* (2006.01)
*A61C 1/07* (2006.01)

(52) U.S. Cl.
CPC ....... *A61C 3/03* (2013.01); *A61B 2017/320072* (2013.01); *A61C 1/07* (2013.01)

(58) Field of Classification Search
CPC .............. A61C 3/03; A61C 1/07; A61C 3/00; A61B 2017/320072
USPC ............ 433/119, 125, 165–166, 86; 606/167, 606/170, 178, 169
See application file for complete search history.

(56) References Cited

U.S. PATENT DOCUMENTS

| | | | | |
|---|---|---|---|---|
| 2,990,616 A | * | 7/1961 | Kuris et al. | 433/119 |
| 3,589,012 A | * | 6/1971 | Richman | 433/86 |
| 4,353,696 A | * | 10/1982 | Bridges | 433/125 |
| 4,571,184 A | * | 2/1986 | Edwardson | 433/166 |
| 4,731,019 A | * | 3/1988 | Martin | 433/119 |
| 5,505,617 A | * | 4/1996 | Skeppmark et al. | 433/118 |
| 5,577,911 A | * | 11/1996 | Garfinkel | 433/119 |
| 5,725,370 A | * | 3/1998 | Himeno et al. | 433/86 |
| D442,690 S | | 5/2001 | Fischer et al. | |
| 6,267,594 B1 | * | 7/2001 | Hugo | 433/119 |
| 2004/0234924 A1 | * | 11/2004 | Hickok et al. | 433/119 |
| 2005/0177184 A1 | | 8/2005 | Easley | |
| 2006/0030797 A1 | | 2/2006 | Zhou et al. | |
| 2006/0068362 A1 | * | 3/2006 | Desrosiers et al. | 433/102 |
| 2007/0275348 A1 | | 11/2007 | Lemon | |
| 2010/0009315 A1 | * | 1/2010 | Striegel et al. | 433/166 |

FOREIGN PATENT DOCUMENTS

DE 102008033062 A1 * 1/2010 ............... A61C 1/07

OTHER PUBLICATIONS

Notification of Transmittal of the International Search Report (Forms PCT/ISA/220 and PCT/ISA/210) and Written Opinion of the International Searching Authority (Form PCT/ISA/237) dated Nov. 29, 2011, issued in the corresponding International Application No. PCT/IB2011/001442.

* cited by examiner

*Primary Examiner* — Heidi M Eide
(74) *Attorney, Agent, or Firm* — Buchanan Ingersoll & Rooney PC (57) ABSTRACT

An ultrasonic tip for minimally invasive crown lengthening, the tip includes a distal end having an external side having a serrated and/or a diamond and/or a rough surface or edge, which extends outward to a cutting edge, and an internal side having a polished area ending in a soft angle with the cutting edge; and a proximal end, which is adapted for mechanical coupling to a surgical handpiece that generates ultrasonic vibrations.

20 Claims, 8 Drawing Sheets

ULTRASONIC TIP FOR MINIMALLY INVASIVE CROWN LENGTHENING

FIELD

The present disclosed dental surgical method and ultrasonic tip refers to a minimally invasive surgical method for crown lengthening, and more particularly to a piezoelectric surgical device used to implement said method, which includes an ultrasonic tip having an external surface or superior surface having an active serrated, diamond and/or a rough surface or edge, which extends outward to a cutting edge, and a relatively rounded and flat polished inferior or internal surface.

BACKGROUND

Dental crown extension or lengthening is an osseous remodeling, used in restorative dentistry to recreate the biologic width and/or to correct the proportions of teeth and gums. Typically, the conventional method or procedure involves a scalloped incision to recreate the proposed gingival height, a gingival flap and approximately two millimeters (2 mm) of bone remodeling, measured from the new gingival margin to preserve the biological width. Bone removal can be carried out with a sharp manual instrument, with a conventional rotating drill or an electric piezosurgery unit.

However, this procedure is by nature, invasive and complex to execute, making the aesthetic results often unpredictable, since repositioning of the gingival flap requires the ability to maintain the planned proposed gingival margin when suturing it to the palate gum. Furthermore, measurements are difficult and inaccurate since the gingival margin is loose the reference points are mobile and there is a permanent risk of tooth damage by using the conventional instruments.

It can be appreciated that the techniques currently in use are effective, but they have not been embraced widely by the dental community, since they require extensive gingival flap elevation associated to postoperative discomfort and high risk of complications, as loss of interproximal papilla, regrowth, swelling, pain, bruising, root sensitivity, root resorption and irreversible root damage. The period of convalescence typically starts from one week, but definitive restoration of the teeth often can only be performed after approximately six months. All of these reasons lead to low acceptance for the patient.

The conventional method cannot be carried out without a gingival flap, because with a blind flapless technique, the required control of the bone depth remodeling does not exist. The instruments or piezoelectric tips used for these operations do not have the dimensions to introduce it under the attached gum without flap elevation nor the option to make the precise removal of 2-3 millimeters of bone tissue from the gingival margin. Moreover, rotating drills or piezoelectric tips act indistinctively on both bone and teeth, such that it is possible to damage the delicate structures of the teeth that the method is intended to enhance.

Accordingly, it would be desirable to have an ultrasonic tip, which can be used with a minimally invasive surgical method for crown lengthening, and which avoids teeth injuries, sutures, and postoperative convalescence periods.

SUMMARY

The ultrasonic tip for minimally invasive crown lengthening has a body, extending between a proximal part adapted for mechanic coupling to a surgical handpiece generating ultrasound vibrations, and a distal part intended to reproduce the ultrasound vibrations transmitted by the handpiece. The frontal distal active part of the tip comprises a semi-circumferential shaped spatula with an active external surface that is serrated, diamond shaped and/or a rough surface or edge, which extends outward to a cutting edge, and an internal surface or back area of the distal part of the tip formed by a relatively flat polished area forming a soft angle of between approximately 5 degrees and approximately 45 degrees with the cutting edge, and more preferably approximately 30 degrees.

In accordance with an exemplary embodiment, an ultrasonic tip for minimally invasive crown lengthening, the tip comprises: a distal end having an external side (or superior or frontal side) having a serrated, a diamond and/or a rough surface or edge, which extends outward to a cutting edge and an internal side (or inferior or back side) having a polished area; and a proximal end, which is adapted for mechanical coupling to a surgical handpiece that generates ultrasonic vibrations.

In accordance with a further exemplary embodiment, a method for minimally invasive crown lengthening comprises: gingival trimming to a desired gingival height by inserting the ultrasonic tip as set forth herein, between a tooth and a corresponding gingiva until reaching an identifier or mark on the tip.

In accordance with another exemplary embodiment, an ultrasonic tip for minimally invasive crown lengthening adapted for mechanic coupling to a surgical handpiece, the tip comprising: an active distal end having a semi-circumferential shaped spatula with a relatively flat back side and an upper side (i.e., superior, front, or external side) of the distal end having a serrated, a diamond and/or a rough surface, that acts selectively on a bone tissue; and wherein a relatively rounded and flat back side of the distal end forms an angle of approximately 5 degrees to approximately 45 degrees with the cutting edge.

In accordance with a further exemplary embodiment, a system for minimally invasive crown lengthening, the system comprises: an ultrasonic generator; a handpiece that is coupled to the ultrasonic generator; and an ultrasonic tip having a distal end having a superior side having an active serrated, a diamond and/or a rough surface or edge, which extends outward to a cutting edge, and a relatively rounded and flat polished inferior surface, and a proximal end, which is coupled to the surgical handpiece.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings are included to provide a further understanding of the disclosed dental surgical method and ultrasonic tip, and are incorporated in and constitute a part of this specification. The drawings illustrate embodiments of the disclosed dental surgical method and ultrasonic tip and, together with the description, serve to explain the principles of the disclosed dental surgical method and ultrasonic tip. In the drawings.

DETAILED DESCRIPTION

An object of the disclosed dental surgical method and ultrasonic tip is to overcome the drawbacks of the prior art through the use of a surgical device combined with a method for minimally invasive crown lengthening. This technology is a device designed for clinical crown lengthening with minimal trauma, and does not detach (create a flap of) gingival tissue. Furthermore, the surgical device avoids injury to the teeth, sutures and the postoperative convalescence period, enabling the patient to continue normally after surgery.

In accordance with an exemplary embodiment, this non-invasive surgical device includes a mechanical coupling insert for a piezoelectric device designed to determine the precise bone removal depth without needing extra measurements and a gingival flap technique making it minimally invasive and also preventing tooth damage and acting selectively on the bone tissue removal.

Figure 1:
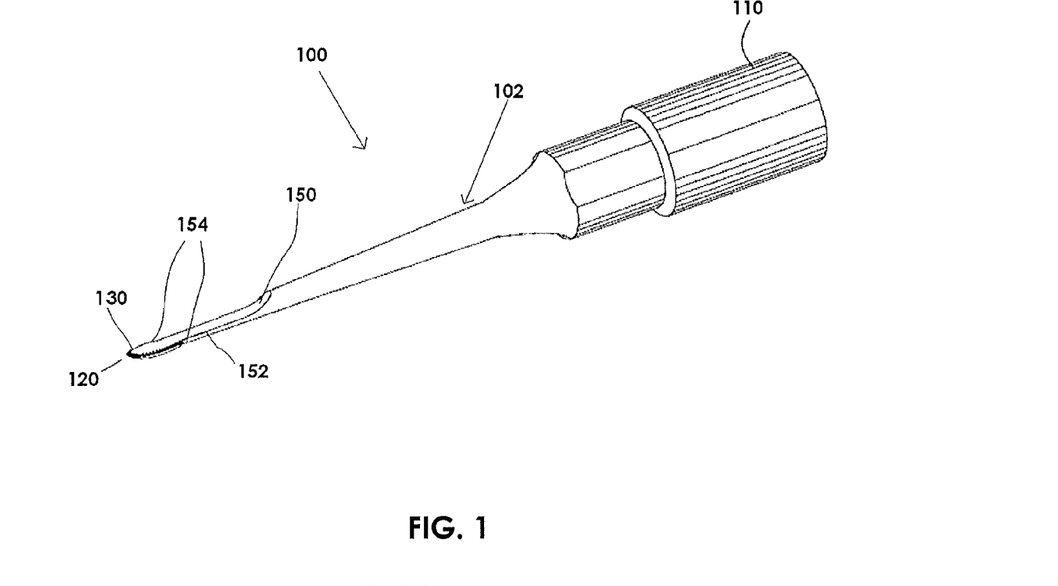
FIG. 1 is a perspective view of an ultrasonic tip for minimally invasive crown lengthening in accordance with an exemplary embodiment.
Figure 3:
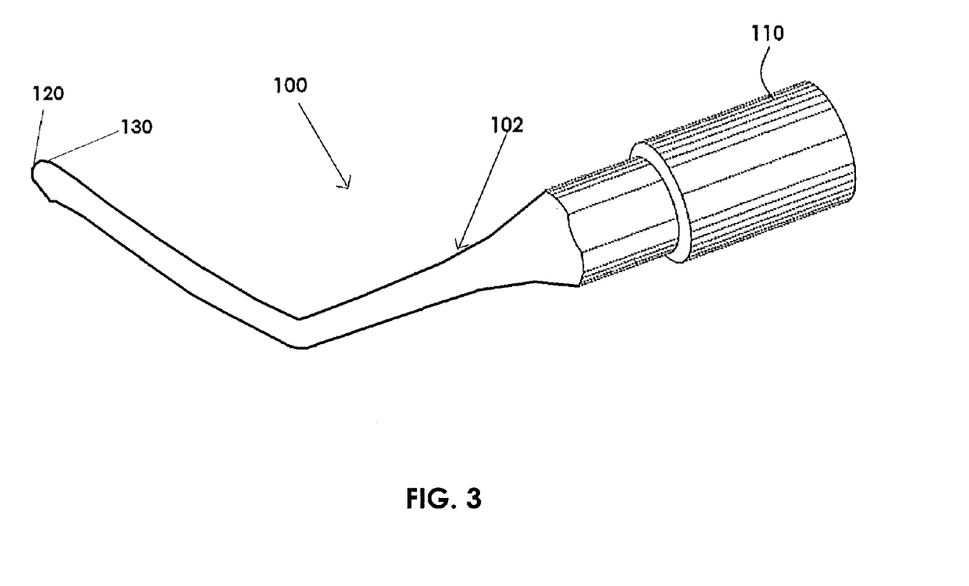
FIG. 3 is a perspective view of the ultrasonic tip for minimally invasive crown lengthening in accordance with another exemplary embodiment.

FIG. 1 is a perspective view of an ultrasonic tip 100 for minimally invasive crown lengthening in accordance with an exemplary embodiment. As shown in FIG. 1, the ultrasonic tip 100 includes a body portion 102, which is preferably relatively straight. However, it can be appreciated that in accordance with an alternative embodiment as shown in FIG. 3, the body portion 102 may vary in angles to facilitate its application to different areas or portions of the mouth. The ultrasonic tip 100 also includes a proximal end (or proximal portion) 110, which is adapted for mechanical coupling to a surgical handpiece that generates ultrasonic vibrations and a distal end 120 (i.e., active surface), which is preferably semi-circumferential shaped or spatula-shaped (i.e., a trapezoid form with rounded ends). In accordance with an exemplary embodiment, the distal end or active surface 120 reproduces the vibrations of the ultrasound handpiece.

Figure 2:
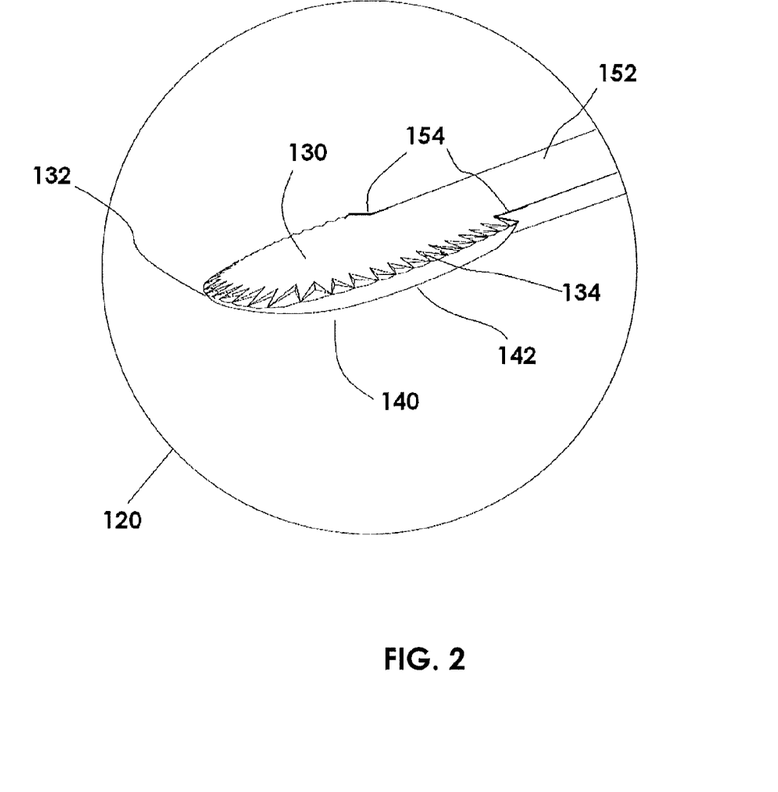
FIG. 2 is a perspective view of the distal end of the ultrasonic tip for minimally invasive crown lengthening as shown in FIG. 1.
Figure 7:
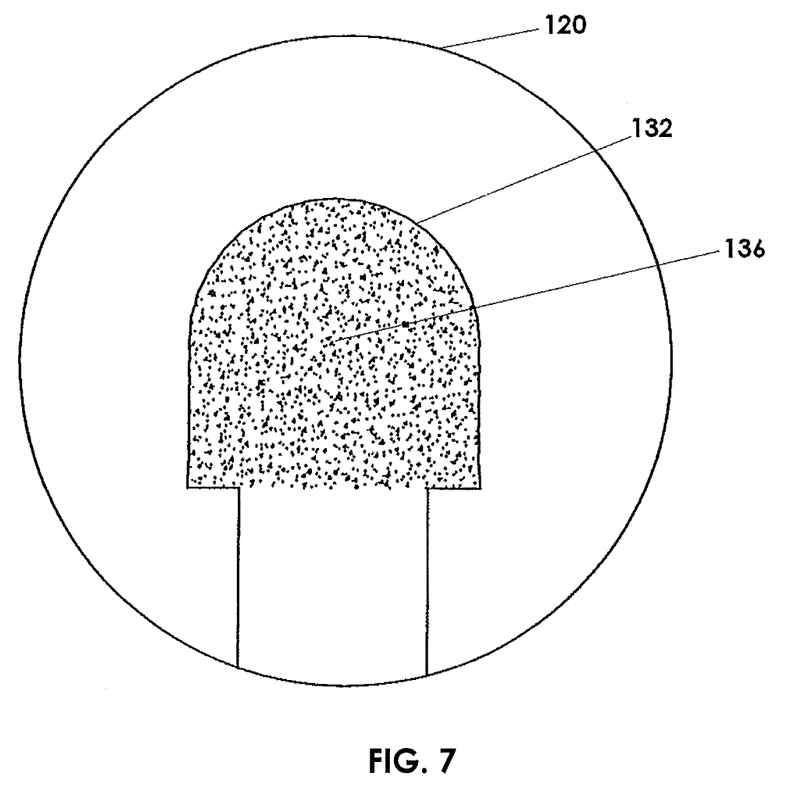
FIG. 7 is a plan view of the distal end of the ultrasonic tip for minimally invasive crown lengthening as shown in FIG. 1 having a semi-circumferential shape, a spatula shape and/or a trapezoid form with rounded ends with a diamonded and/or a rough surface or edge.
Figure 9:
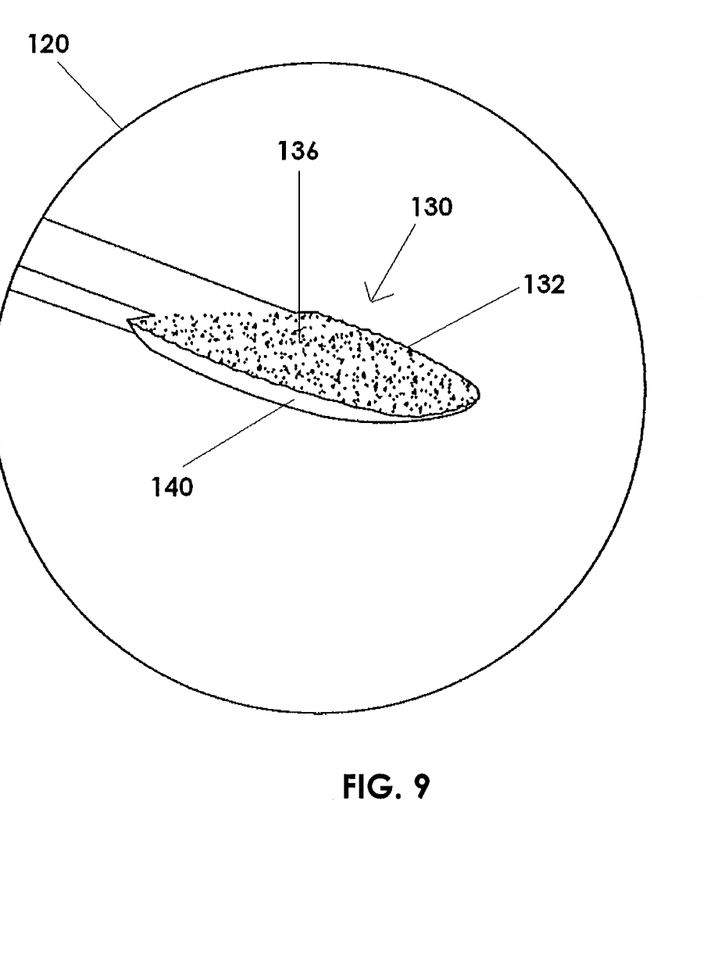
FIG. 9 is a perspective view of the ultrasonic tip for minimally invasive crown lengthening as shown in FIG. 1 having a semi-circumferential shape, a spatula shape and/or a trapezoid form with rounded ends with a diamonded and/or a rough surface or edge.

FIG. 2 is a perspective view of the distal end 120 of the ultrasonic tip 100 for minimally invasive crown lengthening as shown in FIG. 1. As shown in FIG. 2, the external side 130 (i.e., upper surface, superior face, or top side) of the distal end 120 (or spatula-shaped distal end) has preferably a serrated surface 134, which extends outward to a cutting edge 132. Alternatively, the serrated surface 134 can also be diamonded and/or a rough surface or edge 136 (see FIGS. 7 and 9). The internal side (or inferior side) 140 is formed by polished relatively flat, rounded area 142 forming an soft angle of more or less 30 degrees with the cutting edge 132. In accordance with an exemplary embodiment, the distal end 120 has a semi-circumferential shape, a spatula shape and/or a trapezoid form with rounded ends (FIG. 7).

In accordance with an exemplary embodiment, as shown in FIG. 1, the ultrasound tip 100 includes an internal irrigation channel 150 that emerges from a relatively flat base (or straight portion) 152, which is located between the distal end or active surface (i.e., spatula-shaped portion) 120 and the proximal end 110. The distal end or active surface 120 starts from a straight hack or edge 154 that forms an angle of approximately 90 degrees on each side of the distal end 120 of the ultrasonic tip 100. The straight hack or edge 154 serves as a reference, which allows the operator to measure the depth of penetration (insertion) of the distal end 120 (i.e., active surface) of ultrasonic tip (or instrument) 100. In addition, the active surface or distal end 120 allows the operator to accurately quantify bone tissue removal and its relation with the new gingival margin. In accordance with an exemplary embodiment, an outer edge of the active surface 120 (i.e., spatula) begins at the straight hack or edge 154 forming an angle of approximately 90 degrees with the body portion 102 of the ultrasonic tip 100.

It can be appreciated that the ultrasound tip 100 allows an operator to carry out a "blind" technique, which does not require a gingival flap, because of the depth and area of removal is precisely determined by the size of the tip's 100 distal end (or active surface) 120. Moreover, the distal end (or active surface) 120 of the ultrasound tip 100 preferably has a length of approximately 2 mm. However, it can be appreciated that the size of the ultrasonic tip's 100 active surface 120 can be less than and/or greater than approximately 2 mm in length. For example, in accordance with an alternative embodiment, the distal end or active part 120 is approximately 1 mm to 3 mm in length, and more preferably approximately 1.5 mm to 2.5 mm in length, and most preferably approximately 2 mm in length. In accordance with an exemplary embodiment, the distal end has a length of approximately 2 mm with a straight base that forms a bilateral angle of 90 degrees with the body portion and serves as a reference to measure a depth of penetration of the ultrasonic tip 100.

Figure 8:
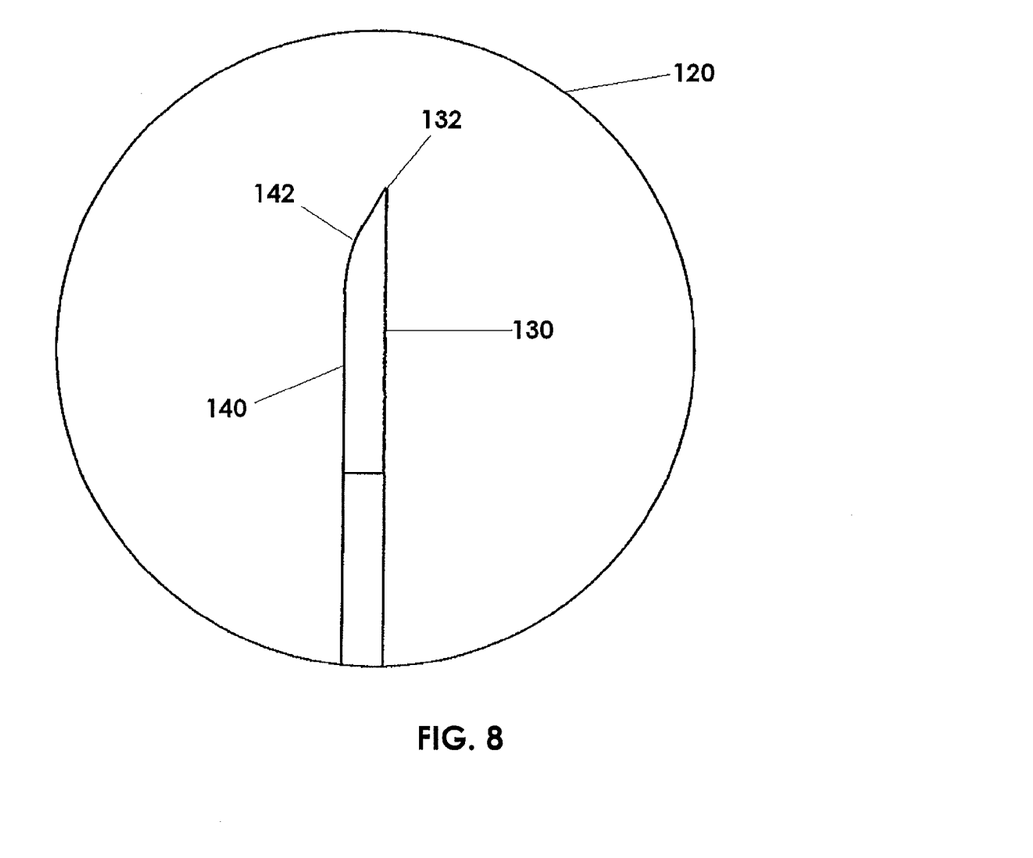
FIG. 8 is a side view of the distal end of the ultrasonic tip for minimally invasive crown lengthening as shown in FIG. 1 having a polished relatively straight or flat surface that forms a soft angle of between approximately 5 degrees and approximately 45 degrees with the cutting edge.

The external side (or superior side) 130 of the ultrasonic tip 100 has a serrated edge 134, diamond and/or rough surface 136 (see FIGS. 7 and 9), which reproduces the vibrations of the electrical handpiece, which allows the ultrasonic tip 100 to selectively remove the bone tissue and maintain the biological width of the gums. In accordance with an exemplary embodiment, the inferior side 140 has a polished relatively straight or flat surface 142 that forms a soft angle of between approximately 5 degrees and approximately 45 degrees with the cutting edge 132, and more preferably approximately 30 degrees (FIG. 8), which avoids damaging the tooth's surface during use.

FIG. 3 is a perspective view of the ultrasonic tip 100 for minimally invasive crown lengthening in accordance with another exemplary embodiment, wherein the body portion 102 varies in angle relative to the proximal end 110 of the ultrasonic tip 100 to facilitate application of the distal end 120 to different areas of a mouth. In accordance with an exemplary embodiment, the body portion 102 can form an angle of between approximately zero (0) degrees (i.e., straight) to 90 degrees with the proximal end 110, and more preferably between approximately zero (0) degrees (i.e., straight) and 60 degrees. By varying the angles, the ultrasonic tip 100 can be used not only on the front teeth but also on the back teeth. The acute and obtuse angles of the tip 100 facilitate access to the mesial, distal, superior or inferior aspects of all teeth. It can be appreciated that the angles are preferably similar to Fischer's Ultra Pack Packer PAT D442.690 REF/UP 171, Ultradent Products Inc., which is incorporated herein by reference.

FIGS. 4(a)-4(d) is series of images showing the use of the ultrasonic tip 100 for crown lengthening. In accordance with an exemplary embodiment, the procedure for using the ultrasonic tip 100 (or ultrasonic coupling insert) for a piezoelectric device for dental crown lengthening includes the steps of trimming the gingival to the desired gingival height, and then introducing the distal end (or active surface) 120 of the ultrasonic tip between the gum and the tooth with the flat inferior side 140 resting against or on the tooth.

Figure 4A:
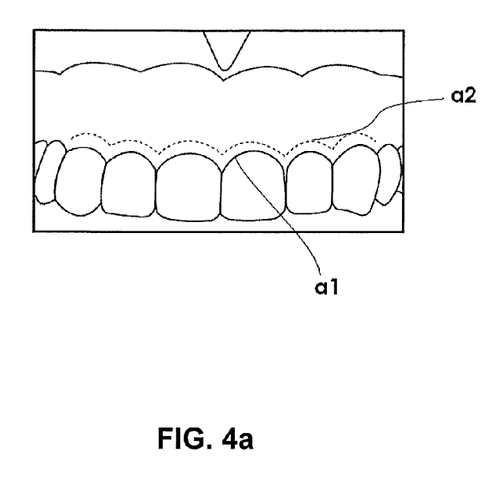
FIG. 4(a) is an image showing a frontal view at the starting point of a desired gingival trim.
Figure 4B:
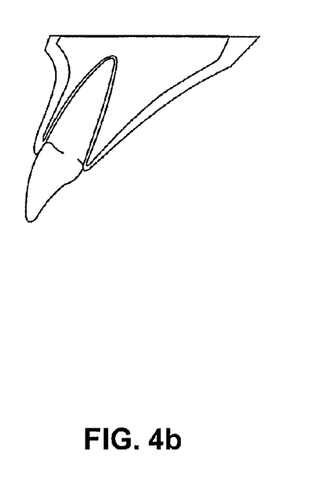
FIG. 4(b) is an image showing a sectional side view of the desired gingival trim.
Figure 4C:
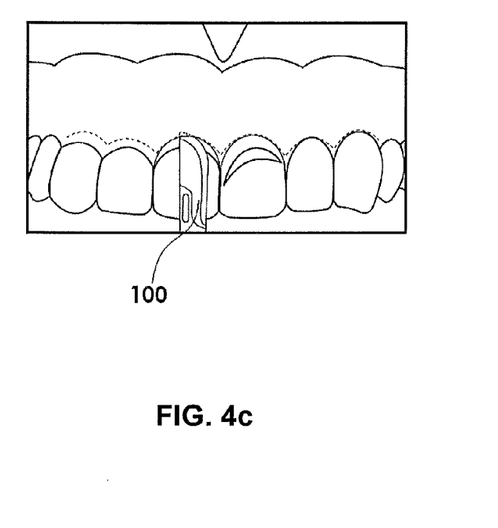
FIG. 4(c) is an image showing a frontal view of the desired gingival trim.
Figure 4D:
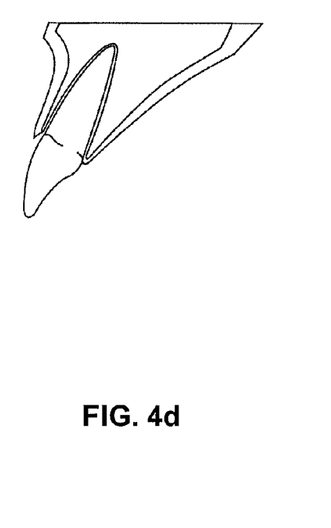
FIG. 4(d) is an image showing a side view of the desired gingival trim.

FIG. 4(a) shows a frontal view of a plurality of teeth and corresponding gingival ("a1") and bone level ("a2") before use of the ultrasonic tip for crown lengthening. FIG. 4(b) is a sectional side view of a tooth and corresponding gingival and bone before removal of the gingival. FIGS. 4(c) and 4(d) show a frontal view of the desired gingival trim and a side view after trimming of the gingiva and bone removal, respectively.

Figure 5A:
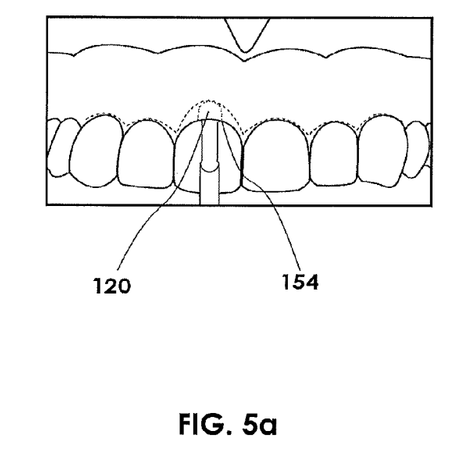
FIG. 5(a) is an image showing the application and use of an ultrasonic tip as shown in FIGS. 1-3 and 7-9, with a surgical handpiece that generates ultrasonic vibrations, such as a piezoelectric device.
Figure 5B:
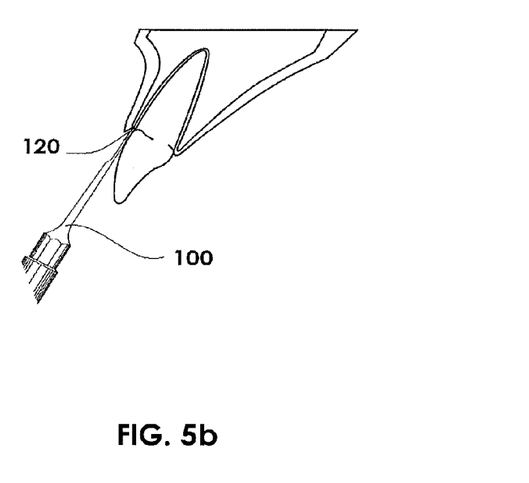
FIG. 5(b) is another image showing the application and use of an ultrasonic tip as shown in FIGS. 1-3 and 7-9, with a surgical handpiece that generates ultrasonic vibrations, such as a piezoelectric device.
Figure 5C:
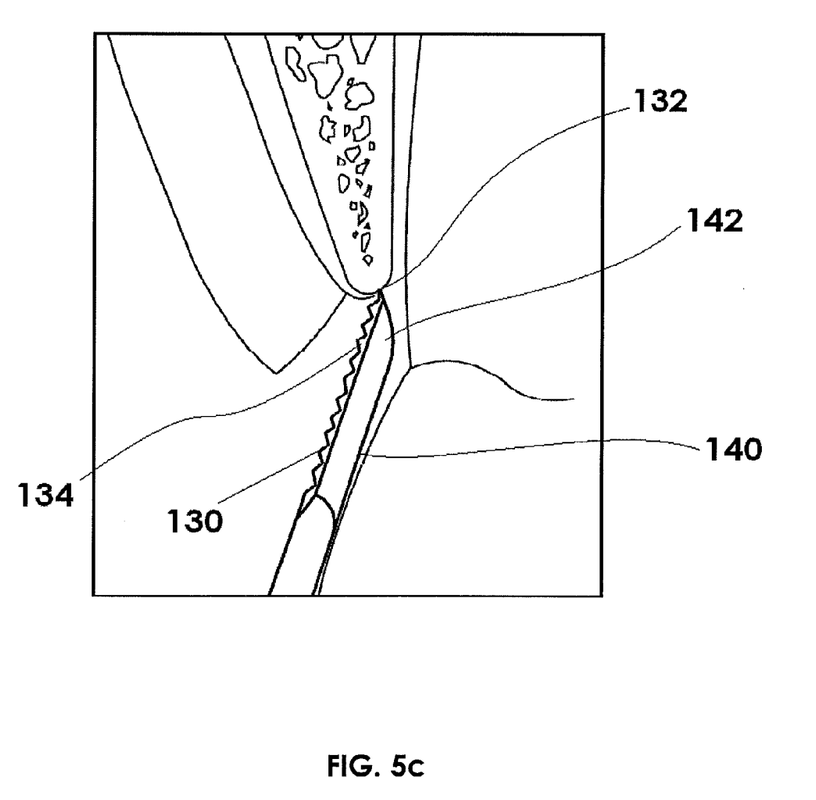
FIG. 5(c) is a further image showing the application and use of an ultrasonic tip as shown in FIGS. 1-3 and 7-9, with a surgical handpiece that generates ultrasonic vibrations, such as a piezoelectric device.

FIGS. 5(a)-(c) show the application and use of an ultrasonic tip 100 as shown in FIGS. 1-4, and described herein with a piezoelectric device or surgical handpiece 210 (FIG. 6) that generates ultrasonic vibrations. FIG. 5(a) is a frontal view of the tooth after gingiva trimming and the bone tissue removal of two millimeters (2 mm), which preferably corresponds, to the size of the ultrasonic tip's distal end or active surface 120. The straight hack base 154 serves as a reference point for depth. FIG. 5(b) shows the corresponding side view of the ultrasonic tip 120 and corresponding bone removal. FIG. 5(c) shows additional detail of the side view, wherein the external surface 130 of the distal end 120 with the active surface 120 for cutting bone tissue, which is towards the gingiva. The relatively flat bottom or polished area 142, which is towards the tooth, forms a soft angle between approximately 5 degrees and approximately 45 degrees with the cutting edge 132, and more preferably at approximately 30 degrees with the cutting edge 132 (see FIG. 8). It can be appreciated that by angling the polished area 142 of the inferior side 140 at an angle of approximately 5 to approximately 45 degrees with the cutting edge 132, the ultrasonic tip 100 does not damage the tooth during cutting of the gingival.

Figure 6:
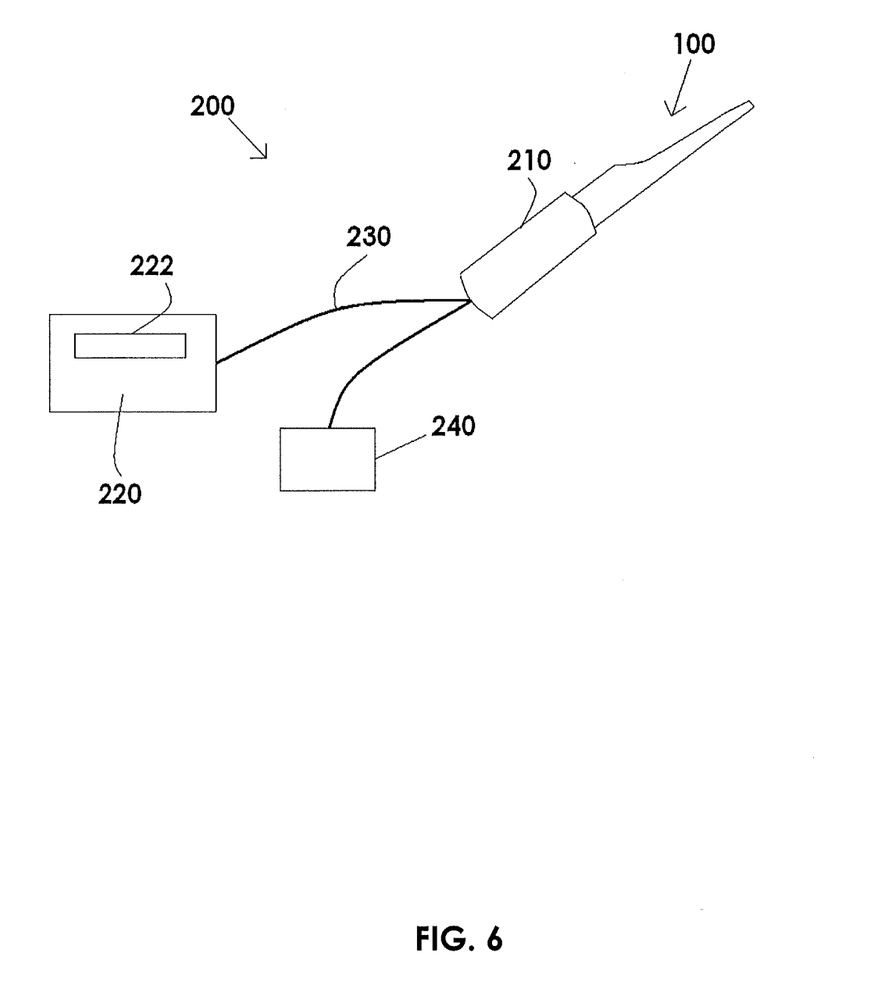
FIG. 6 is a diagram of a system for a minimally invasive surgical method for crown lengthening, which includes a piezoelectric surgical device in accordance with an exemplary embodiment.

FIG. 6 is a diagram of a system 200 for a minimally invasive surgical method for crown lengthening, which includes a piezoelectric surgical device in accordance with an exemplary embodiment. As shown in FIG. 6, the system 200 includes an ultrasonic tip 100, a surgical handpiece 210, an ultrasonic generator 220, and a coupling member or cable 230, which couples the ultrasonic generator 220 to the surgical handpiece 210. The ultrasonic generator 220 generates a source of energy or ultrasonic energy, which is transmitted to the handpiece 210 to generate ultrasonic vibrations, and which can be reproduced by the ultrasonic tip 100. The ultrasonic generator 220 preferably includes a display/controller unit 222 having circuit boards and software (not shown). The system 200 also preferably includes a source of liquid or a liquid reservoir 240, which is fed to the internal irrigation channel 150.

It can be appreciated that the ultrasonic generator 220 can be any suitable generator or ultrasonic generator used in periodontal medicine and general dentistry, including such generators as disclosed in U.S. Patent Publication Nos. 20090162810, 20090202961, 20100124732, and 20110020765, which are incorporated herein by reference in their entirety Table No. 1 presents the comparison between the conventional procedure for clinical crown lengthening of the teeth and the minimally invasive procedure with an ultrasonic tip as shown in FIGS. 1-6, and the corresponding benefits of the ultrasonic tip as compared to what is known in the state of the art.

TABLE NO. 1

| ACTION | OSTEOPLASTY | PLASTIA MINIMALLY INVASIVE WITH PIEZO ELECTRIC |
| --- | --- | --- |
| Planning Time | 1 hr | 15 minutes |
| Duration of surgery | 3 hr | 20 minutes |
| Type of surgery | Invasive with elevation (detachment) of the gingival flap | Not invasive, with out gingival flap detachment (flapless) |
| Precision | Needs of great skill and training of the operator | Independent from the operator's skill |
| Sutures | Multiple | Not required |
| Convalescence | Seven months | No |
| Rehabilitation Period | Six months | One month |
| Papilla Loss | Frequently | Rarely |
| Over correction | Possible | Rarely |
| Pain, Bruising | Frequently | Rarely |

It will be understood that the foregoing description is of the preferred embodiments, and is, therefore, merely representative of the article and methods of manufacturing the same. It can be appreciated that many variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. An ultrasonic tip for minimally invasive crown lengthening, the ultrasonic tip comprising:
   a distal end with an external side, an internal side, and a cutting edge;
   a proximal end adapted for mechanical coupling to a surgical handpiece that provides ultrasonic vibrations; and
   a body portion extending in a longitudinal direction from the proximal end towards the distal end,
   wherein the distal end has a longer longitudinal axis parallel to an axis of the body portion, and a shorter transverse axis orthogonal to the longitudinal axis, the longitudinal and transverse axes defining a plane, wherein the external side of the distal end comprises a serrated edge and a diamond and/or rough surface extending outward from the longitudinal axis substantially parallel to the plane, an entirety of the external side of the distal end associated with the cutting edge being the diamond and/or rough surface, wherein the internal side of the distal end comprises a polished surface extending outward by smoothly and continuously tapering in a direction along the longitudinal axis away from a proximal-most portion of the distal end towards a distal-most portion of the distal end, wherein the polished surface of the internal side of the distal end also extends in a direction along the transverse axis from the longitudinal axis by smoothly and continuously tapering from the longitudinal axis to the cutting edge, wherein the external side and the smoothly and continuously tapering internal side form an acute angle at the cutting edge, and wherein a straight base of the distal end extends away from longitudinal sides of the body portion.

2. The tip of claim 1, wherein the straight base of the distal end forms a substantially right angle with the body portion, the straight base being configured to measure depth of penetration of the ultrasonic tip.

3. The tip of claim 2, wherein the body portion varies in angle relative to the proximal end of the ultrasonic tip to facilitate application of the distal end to different areas of a mouth.

4. The tip of claim 2, wherein the body portion comprises an internal irrigation channel that emerges from a flat portion of the body portion of the ultrasonic tip.

5. The tip of claim 2, wherein the distal end has a length of approximately 2 mm with the straight base that forms a bilateral angle of 90 degrees with the body portion and serves as a reference to measure a depth of penetration of the ultrasonic tip.

6. The tip of claim 1, wherein the distal end has a semi-circumferential shape or a trapezoid form with rounded ends.

7. The tip of claim 1, wherein the internal side forms an angle of approximately 5 degrees to approximately 45 degrees with the cutting edge.

8. The ultrasonic tip of claim 1, wherein the polished surface of the distal end forms a soft angle of approximately 30 degrees with the cutting edge.

9. A method for minimally invasive crown lengthening without a tissue flap comprising:
   trimming the gingiva to a desired gingival height; and
   inserting an ultrasonic tip according to claim 1, between a tooth and a corresponding gingiva until reaching an identifier on the ultrasonic tip.

10. The method of claim 9, wherein the identifier is the straight base of the distal end that forms a bilateral angle of 90 degrees with the body portion of the tip.

11. The method of claim 9, further comprising placing the internal side against the tooth and the external side against the gingiva.

12. The method of claim 11, further comprising coupling the ultrasonic tip to at least one piezoelectric device.

13. The method of claim 12, further comprising maintaining a biological width by removing no greater than 2 to 3 mm of bone from a new gingival height.

14. The method of claim 9, wherein an active surface of the ultrasonic tip defines a removal depth and a removal area.

15. An ultrasonic tip for minimally invasive crown lengthening adapted for mechanically coupling to a surgical handpiece, the tip comprising:
   an active distal end having a semi-circumferential shaped spatula with a relatively flat back side, an upper side, a straight base, and a cutting edge, the active distal end further having a central portion defined by a largest distance between the relatively flat back side and the upper side; and
   a body portion extending from a proximal end towards the active distal end, the body portion having a longitudinal extent,
   wherein the active distal end has a first axis extending in a direction of the longitudinal extent of the body portion and a second axis extending substantially orthogonal to the first axis, the active distal end having a greater extent along the first axis than in the second axis, the first axis and the second axis of the active distal end defining a plane,
   wherein the straight base of the active distal end extends outwardly from each side of the body portion substantially along the second axis,
   wherein an entire surface of the upper side of the active distal end associated with the cutting edge is a diamond and/or a rough surface extending outward to the cutting edge that acts selectively on bone tissue, the upper side of the active distal end extending substantially parallel to the plane,
   wherein the relatively flat back side of the active distal end extends outward along the first axis by smoothly and continuously tapering away from a portion of the active distal end directly adjacent the body portion towards the upper side to meet with the cutting edge,
   wherein the relatively flat back side of the active distal end further extends outward along the second axis by smoothly and continuously tapering away from the central portion towards the upper side to meet with the cutting edge at a first portion and a second portion, the relatively flat back side smoothly and continuously tapering at an angle of approximately 5 degrees to approximately 45 degrees towards the upper side to meet with the cutting edge, and
   wherein the first and second portions of the cutting edge are spaced from each other on opposite sides of the central portion along the second axis.

16. The ultrasonic tip of claim 15, wherein the relatively flat back side of the active distal end is polished.

17. The ultrasonic tip of claim 15, wherein the active distal end is approximately 2 mm in length.

18. The ultrasonic tip of claim 15, wherein the active distal end is approximately 1.5 mm to approximately 3 mm in length.

19. A system for minimally invasive crown lengthening without a tissue flap, the system comprising:
   an ultrasonic generator;
   a handpiece that is coupled to the ultrasonic generator;
   an ultrasonic tip having a distal end having a superior side, an inferior side with a polished area, and a cutting edge; and
   a body piece having a longitudinal extent extending from the handpiece towards the distal end,
   wherein the distal end extends further in a direction along the longitudinal extent of the body piece than in a direction orthogonal to the longitudinal extent of the body piece, the direction along the longitudinal extent of the body piece and the direction orthogonal to the longitudinal extent of the body piece defining a plane of the distal end, the distal end having a straight base that extends away from sides of the body portion in the direction substantially orthogonal to the longitudinal extent of the body piece, wherein the superior side comprises a serrated edge and a diamonded and/or rough surface extending outward in a plane substantially parallel to the plane of the distal end to the cutting edge, the superior side being associated with the cutting edge, the superior side being entirely formed by the diamonded and/or rough surface, wherein the inferior side polished area defines a surface that smoothly and continuously tapers away from a proximal-most end of the distal end towards the superior side to the cutting edge in the direction along the longitudinal extent, and wherein the polished area smoothly and continuously tapers away from a thickest portion of the distal end towards the superior side to the cutting edge by smoothly and continuously tapering in the direction orthogonal to the longitudinal extent of the body piece towards the superior side to the cutting edge to a first portion of the cutting edge and by smoothly and continuously tapering towards the superior side to a second portion of the cutting edge, the first portion of the cutting edge being opposite the second portion of the cutting edge.

20. The system of claim 19, further comprising a source liquid, which is fed to an irrigation channel within the ultrasonic tip.

* * * * *